United States Patent
Kuzuhara et al.

(10) Patent No.: US 7,402,685 B2
(45) Date of Patent: Jul. 22, 2008

(54) PROCESS OF PRODUCING DIOXANE GLYCOL

(75) Inventors: Ikutaro Kuzuhara, Okayama (JP); Yutaka Nakamura, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 1 day.

(21) Appl. No.: 11/541,531

(22) Filed: Oct. 3, 2006

(65) Prior Publication Data

US 2007/0078270 A1 Apr. 5, 2007

(30) Foreign Application Priority Data

Oct. 4, 2005 (JP) ............................. 2005-291603

(51) Int. Cl.
*C07D 319/06* (2006.01)
(52) U.S. Cl. ..................................................... 549/374
(58) Field of Classification Search .................. 549/374
See application file for complete search history.

(56) References Cited

U.S. PATENT DOCUMENTS 2,945,008 A 7/1960 Caldwell et al.

FOREIGN PATENT DOCUMENTS

JP 59-148776 8/1984

OTHER PUBLICATIONS

Galiano, et al., "Formation of 1,3-Dioxanes in Water", Journal of Organic Chemistry, vol. 29, No. 11, 1964, pp. 3424-3426.
European Search Report in connection with European Patent Application No. 06121493.8, dated Oct. 5, 2007.

*Primary Examiner*—Bernard Dentz
(74) *Attorney, Agent, or Firm*—Antonelli, Terry, Stout & Kraus, LLP.

(57) ABSTRACT

A production method of 2-(5-ethyl-5-hydroxymethyl-1,3-dioxane-2-yl)-2-methylpropane-1-ol (DOG) which includes a step of acetalizing hydroxypivalaldehyde with trimethylolpropane in a solvent in the presence of an acid catalyst. After the acetalization, the reaction product liquid is neutralized and then heated to dissolve the deposited DOG crystals. Then, the reaction product liquid is cooled to recrystallize DOG. DOG produced in such manner has an adequately large particle size. Therefore, DOG is easy to handle and involves little danger of dust explosion.

11 Claims, No Drawings

PROCESS OF PRODUCING DIOXANE GLYCOL

BACKGROUND OF THE INVENTION

1. Field of the Invention

The present invention relates to a process of producing 2-(5-ethyl-5-hydroxymethyl-1,3-dioxane-2-yl)-2-methyl-propane-1-ol (hereinafter referred to as "dioxane glycol" or "DOG"), which is represented by the following formula I:

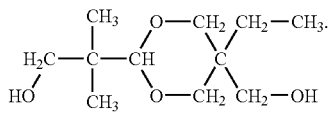
(I)

2. Description of the Prior Art

DOG is produced, for example, by a process including the acetalization of hydroxypivalaldehyde (hereinafter referred to as "HPA") represented by the following formula II:

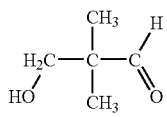
(II)

with trimethylolpropane (hereinafter referred to as "TMP") represented by the following formula III:

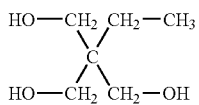
(III)

in the presence of an acid catalyst; and the filtration, washing and drying of DOG crystals precipitated in the reaction product liquid (JP 62-59104B).

The particle size of DOG crystals produced by the process of JP 62-59104B is as extremely small as 10 μm or less. Therefore, the solid-liquid separation after the reaction takes a long time, to reduce the efficiency of the solid-liquid separation. In addition, since the wet cake obtained by the solid-liquid separation has a high liquid content, a long time is required for drying, to reduce the efficiency of drying. DOG having a small particle size is easy to form dust, to make the handling thereof difficult. Additionally, since DOG having a small particle size which has been produced by known methods is electrostatically charged quite easily, there is a strong possibility of dust explosion.

However, the documents describing known production methods are completely silent about the increase in the particle size of DOG, and therefore, it has been desired to develop a process of producing DOG having a larger particle size. The particle size of DOG crystals produced by known methods can be increased by a purification such as recrystallization. Such measure is, however, industrially disadvantageous, because not only additional chemicals, apparatuses, etc. are required, but also the number of steps for the production of DOG is increased.

DOG has the following two isomers: trans isomer and cis isomer.

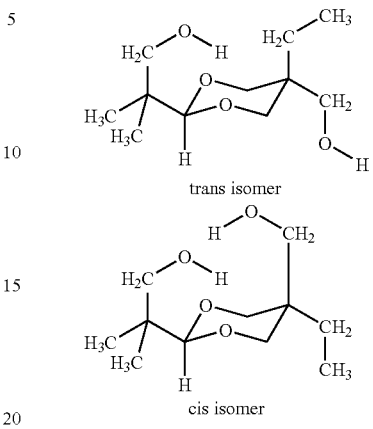

trans isomer cis isomer

DOG or its derivative composed of a mixture of the trans isomer and cis isomer is not suitable as the raw material for industrial use, because products having poor properties are produced. Therefore, DOG is required to have a high content of the trans isomer (hereinafter referred to as "high trans-isomer purity" or merely "high purity").

However, the documents describing known production methods are completely silent about the isomer purity of DOG. As a result of extensive studies by the inventors, it has been found that DOG produced by known methods has a low trans-isomer purity, although mainly composed of the trans isomer. For example, the highest melting point of DOGs actually disclosed in the working examples of JP 62-59104B is 121.5° C. However, a purified DOG having a trans-isomer purity of 99% or more, which is obtained by the recrystallization from acetone of DOG having such highest melting point, shows a melting point of 125° C. or higher.

As described above, although the purity of DOG produced by known methods can be increased by purification such as recrystallization, such measure is industrially disadvantageous, because not only additional chemicals, apparatuses, etc. are required, but also the number of steps for the production of DOG is increased.

SUMMARY OF THE INVENTION

An object of the present invention is to solve the problems associated with the conventional techniques and to provide a process of producing DOG (high purity DOG) having a high trans-isomer purity, which is easy to handle in the industrial operations because of its adequately large crystal particle size and involves little danger of dust explosion.

The inventors have made extensive studies in view of obtaining the above high purity DOG having an adequately large crystal particle size without using a purification step. As a result, it has been found that the high purity DOG having an increased crystal particle size can be easily produced by sequential steps of neutralizing an acid catalyst after the reaction of HPA and TMP; dissolving all or a part of DOG crystals by heating the reaction production liquid; cooling the reaction product liquid; and separating DOG crystals. It has been further found that DOG having a high trans-isomer purity can be easily produced by performing the reaction in a solvent in the presence of an acid catalyst while adding either one of HPA solution and TMP (solid or solution) to the other. The present invention is based on these findings.

Thus, the present invention provides a process of producing a dioxane glycol represented by the following formula I:

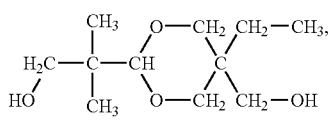  (I)

which includes:
(1) a step of allowing hydroxypivalaldehyde represented by the following formula II:

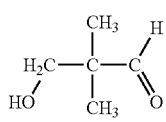  (II)

to react with trimethylolpropane represented by the following formula III:

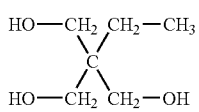  (III)

in a solvent in the presence of an acid catalyst, thereby obtaining a reaction product liquid containing the dioxane glycol of the formula I;
(2) a step of neutralizing the reaction product liquid;
(3) a step of heating the reaction product liquid after the neutralization to 70° C. or higher, thereby completely or partly dissolving crystals of the dioxane glycol; and
(4) a step of cooling the reaction product liquid after the heating to 60° C. or lower, thereby allowing the dissolved dioxane glycol to recrystallize;

while regulating X represented by the following formula:

$X(\%\ by\ weight)=B/A\times100$ wherein A is a total weight of the reaction product liquid obtained in the step 1 and B is a theoretical amount of the dioxane glycol to be produced from hydroxypivalaldehyde and trimethylolpropane which are introduced into a reaction system, within a range of from 3 to 35% by weight.

According to the present invention, DOG having a high trans-isomer purity which is easy to handle is obtained. Such high purity DOG is useful as raw materials for the production of polymer materials and chemical products. Therefore, the present invention has a great industrial significance.

DETAILED DESCRIPTION OF THE INVENTION

In the present invention, the high purity DOG is produced by the reaction of TMP and HPA in the presence of an acid catalyst. Commercially available TMP may be used as-purchased or after purification by distillation or crystallization. TMP may be used in the reaction in the form of a solid or a solution in water, an organic solvent or a mixed solvent of an organic solvent and water, with an aqueous solution being preferred. Examples of the organic solvent include alcohols and ethers. The concentration of TMP in TMP solution is preferably from 10 to 99% by weight.

HPA to be used in the reaction may be HPA solution prepared by the reaction of isobutylaldehyde and formaldehyde (formalin) or may be a purified HPA obtained by a known method such as a crystallization from water. The concentration of formaldehyde in HPA is preferably 2.2% by weight or less and more preferably 1% by weight or less. When being 2.2% by weight or less, the formation of the cis isomer is prevented and the effect of increasing the particle size is sufficiently obtained. HPA is used in the reaction in the form of a solution in water, an organic solvent or a mixed solvent of an organic solvent and water. Examples of the organic solvent include alcohols and ethers. The concentration of HPA in HPA solution is preferably from 10 to 99% by weight.

The solvent for the reaction of HPA and TMP is water, an organic solvent or a mixed solvent of an organic solvent and water, with water being preferred. Examples of the organic solvent include alcohols and ethers such as methanol, ethanol, propanol, tetrahydrofuran and 1,4-dioxane.

The molar ratio, HPA/TMP, is preferably from 0.7 to 2.5, more preferably from 0.9 to 1.5, and still more preferably 1 to 1.3. When being 2.5 or less, the side reaction such as decomposition of excess HPA and dimerization of HPA is prevented, and the increase of the material unit of HPA (amount of HPA required for the production of a unit amount of DOG) and the reduction of the purity of DOG are avoided. DOG is highly soluble in a solution rich in TMP, and therefore, a substantial portion of the produced DOG comes to dissolve in the mother liquor to drastically reduce the yield of DOG, if TMP is used in an excessively large amount as compared with HPA. This problem can be avoided when HPA/TMP is 0.7 or more.

Examples of the acid catalyst include, but not limited to, mineral acids such as hydrochloric acid, sulfuric acid, phosphoric acid and nitric acid, and organic acids such as benzenesulfonic acid, toluenesulfonic acid and methanesulfonic acid, with hydrochloric acid being particularly preferred. The amount of the acid catalyst to be used in the reaction depends upon its kind, and is selected so as to maintain the pH of the reaction system in a range preferably from 0.1 to 3, more preferably from 0.2 to 2.5, and still more preferably from 0.3 to 2. Within the above range, the corrosion of apparatus and decrease in the reactivity are prevented, and the reductions in the yield and trans-isomer purity of DOG are prevented.

In the present invention, the raw materials (HPA, TMP, acid catalyst and solvent) may be all charged in a reaction vessel simultaneously and then the acetalization is performed. Preferably, the acetalization is performed while adding HPA solution to TMP (solid or solution), or adding TMP (solid or solution) to HPA solution. For example, the acetalization of HPA with TMP is preferably performed by any one of the following methods:
(1) Method in which HPA solution is added continuously (supply with a pause of less than 5 s) or intermittently (supply with a pause of 5 s or longer) to TMP solution containing the acid catalyst which has been heated in advance to a temperature around the reaction temperature (described below);
(2) Method in which HPA solution and the acid catalyst, which are kept apart from each other, are simultaneously added dropwise, in either continuous or intermittent manner, to TMP solution which has been heated in advance to a temperature around the reaction temperature;

(3) Method in which TMP (solid or solution) and the acid catalyst, which are kept apart from each other, are simultaneously added dropwise, in either continuous or intermittent manner, to HPA solution which has been heated in advance to a temperature around the reaction temperature; and (4) Method in which a mixture of TMP (solid or solution) and the acid catalyst is continuously or intermittently added to HPA solution.

The reaction temperature is preferably from 40 to 60° C. and more preferably from 50 to 60° C. The variation of temperature during the reaction is preferably controlled within ±5° C. Within the above range, the reaction time does not become so long and DOG having a high trans-isomer purity is obtained. Although the reaction pressure is not specifically limited, it is industrially practical to perform the reaction under atmospheric pressure. The term "trans-isomer purity" referred to herein is the proportion (% by weight) of the trans isomer to the total weight of DOG.

In the methods 1 to 4 described above, the addition or dropwise addition is carried out preferably over 0.5 to 24 h, more preferably over 1 to 12 h, and still more preferably over 1.5 to 6 h. Within the above range, DOG having a high trans-isomer purity is produced in high yields without spending much time. The rate of addition or dropwise addition is determined by the selected HPA/TMP (molar ratio) and period of time for the addition or dropwise addition. The rate may be constant during the addition or dropwise addition or may be changed.

In the present invention, HPA, TMP, acid catalyst and solvent are charged and supplied so as to regulate X represented by the following formula:

$$X(\% \text{ by weight}) = B/A \times 100$$

wherein A is the total weight of the acid catalyst, HPA, TMP and the solvent (inclusive of the solvents for HPA solution and TMP solution and the reaction solvent) which are supplied to the reaction system, i.e., the total weight of the reaction product liquid at the time of completing the reaction of HPA and TMP, and B is a theoretical amount of DOG to be produced from HPA and TMP which are introduced into the reaction system, within a range of preferably from 3 to 35% by weight, more preferably from 10 to 30% by weight, and still more preferably from 13 to 25% by weight. X corresponds to the concentration of DOG in the reaction product liquid when the reaction proceeds theoretically. In the method of the present invention, since a substantial portion of produced DOG deposits as crystals, X is nearly the same as the concentration of DOG crystals in the reaction product liquid at the completion of the reaction. When X is 3% by weight or more, the production amount of DOG per a single run of reaction is prevented from being lowered. When being 35% by weight or less, the crystal concentration in the reaction product solution is moderate for a sufficient stirring of the reaction system, to increase the trans-isomer purity of DOG to 98% by weight or more. In addition, the transfer of the reaction product liquid is easy, to enhance the production efficiency.

After completion of the dropwise addition and before neutralization, the reaction product liquid may be aged preferably for 0.5 to 12 h, more preferably for 1 to 8 h, and still more preferably for 1.5 to 6 h at a temperature nearly the same as the reaction temperature. By the aging within the above range of time, the reaction proceeds sufficiently without spending much time, to increase the yield of DOG.

After completion of the DOG synthesis reaction, the reaction product liquid is neutralized. Examples of the alkali for the neutralization include, but not limited to, metal hydroxides such as sodium hydroxide, potassium hydroxide and calcium hydroxide, and carbonates such as sodium carbonate, sodium hydrogencarbonate and potassium carbonate. The pH of the reaction product liquid after neutralization is preferably from 4 to 11, more preferably from 5 to 10, and still more preferably from 6 to 9. When the pH is 4 or more, a high yield and purity of DOG are obtained because the decomposition of DOG is prevented in the next heat treatment, and the particle size is increased to a range preferably 15 to 200 μm, more preferably 20 to 200 μm. When being 11 or less, the side reaction is prevented. Since the neutralization is exothermic, the temperature for the neutralization is preferably equal to the reaction temperature or lower, and more preferably from 30 to 50° C.

After the neutralization, the reaction product liquid is heated to preferably 70° C. or higher, more preferably from 80 to 105° C., and still more preferably from 90 to 105° C. so as to allow all or a part of the deposited DOG crystals to dissolve. The rate of temperature rise is preferably from 0.1 to 10° C./min. The heating is continued preferably until the concentration of DOG crystals remaining not dissolved in the reaction product solution reaches 15% by weight or less, and more preferably until all DOG crystals are dissolved. If the heating is stopped before the concentration of DOG crystals reaches 15% by weight or less, the effect of increasing the particle size is not sufficient. The time for heating is not specifically limited.

After confirming the dissolution of a part or all of DOG crystals, the reaction product solution is cooled preferably under stirring to allow DOG to recrystallize. The stirring rate expressed by the circumferential speed of stirring blade tip is preferably 0.5 m/s or more and more preferably 0.7 m/s or more. In an industrial operation of the present invention using a 100-L or larger reaction vessel, the circumferential speed is still more preferably 1 m/s or more to ensure a sufficient stirring. When the circumferential speed is 0.5 m/s or more, DOG crystals formed by cooling are prevented from being excessively aggregated, to facilitate the operation of solid-liquid separation and enable the production of a high purity DOG with a small liquid content. An excessively high circumferential speed is not required, and a circumferential speed up to the level which can be achieved in the practical industrial operation, for example, about 15 m/s, is sufficient for the purpose. Since the viscosity of the reaction product liquid is not extremely high, the shape and number of the stirring blades are not specifically limited. The recommended diameter of the stirring blade is 5% or more of the inner diameter of reaction vessel. The shape of reaction vessel is also not specifically limited, and it is recommended to use a general baffle plate, etc. thereby to enhance the stirring efficiency.

The cooing temperature for the recrystallization of DOG is preferably from 60 to 20° C., more preferably from 45 to 25° C., and still more preferably from 40 to 30° C. The recrystallization is perfected when the temperature is 60° C. or lower, to increase the yield of DOG. When being 20° C. or higher, a high purity DOG is produced without needing a specific equipment. The cooling rate is preferably from 0.1 to 10° C./min. The time for cooling is not limited as far as the recrystallization is completed.

DOG crystals are separated from the reaction product liquid by filtration or centrifugal separation. After the separation into DOG crystals and the mother liquor, DOG crystals are generally washed with a solvent of the same kind as used in the reaction. The separated DOG crystals are dried by direct heating, indirect heating or vacuum drying to obtain the final product.

The present invention will be described in more detail. However, it should be noted that the scope of the present invention is not limited thereto. The measurements were conducted by the following methods.

(1) Analysis of HPA by gas chromatography (GC)

An acetone solution of crude HPA was analyzed using a capillary column (product equivalent to "DB-1" of Agilent Technologies Inc.).

(2) Trans-isomer purity of DOG

An acetone solution of DOG was analyzed using a capillary column (product equivalent to "DB-1" of Agilent Technologies Inc.). The trans-isomer purity was calculated from the peak areas of the gas chromatogram.

(3) Particle size of DOG

Measured using a particle size distribution analyzer "HELOS KFS" manufactured by SYMPATEC Inc.

EXAMPLE 1

Into a mixture of 601 parts by weight of isobutylaldehyde (IBD) and 657 parts by weight of 37% by weight formalin, 33 parts by weight of triethylamine (TEA) was added over 5 min at 40° C. with stirring under a stream of nitrogen. The temperature of the reaction liquid reached 65° C. at the time the addition of TEA was completed. The temperature was gradually increased and reached 90° C. after 30 min. The reaction was allowed to continue at 90° C. for 5 min, and then stopped by external cooling to 60° C. The low boiling components such as non-reacted IBD and TEA and methanol ware removed by distillation at 60 to 70° C. under 53 kPa, to obtain 1191 parts by weight of a reaction product solution containing HPA (crude HPA). It was found by GC analysis that the crude HPA contained 62.4% by weight of HPA, 0.3% by weight of IBD, 0.3% by weight of TEA, 0.6% by weight of neopentyl glycol, 2.0% by weight of mononeopentyl glycol hydroxypivalate, and 28.5% by weight of water.

After mixing 1191 parts by weight of the above crude HPA with 3825 parts by weight of water, 916 parts by weight of TMP and 100 parts by weight of concentrated hydrochloric acid, the reaction was allowed to proceed at 60° C. for 5 h. After the reaction, the reaction product liquid was cooled to 40° C. and neutralized with an aqueous 25% sodium hydroxide to pH 7. After the neutralization, the reaction product liquid was heated to 100° C., where all of DOG crystals were found to be dissolved. Then, the reaction product liquid was cooled to 50° C. with stirring for one hour while increasing the circumferential speed of a paddle stirring blade up to 1.3 m/s, to recrystallize the dissolved DOG. The reaction product liquid was centrifugally separated, and the separated DOG crystals were washed with 1520 parts by weight of water and then the water was sufficiently removed, to obtain 1406 parts by weight of wet DOG crystals. By vacuum-drying the wet DOG crystals, 1237 parts by weight of dried DOG was obtained. X was 21% by weight and the yield of DOG on the basis of the charged TMP was 83 mol %. The water content of the wet DOG crystals before drying was 12% (wet basis) and the average particle size of DOG obtained was 25 μm. The melting point of DOG obtained was 124.5° C. and the trans-isomer purity determined by GC analysis was 98.5%.

COMPARATIVE EXAMPLE 1

The procedures of Example 1 were repeated except for centrifugally separating the reaction product liquid without heating after the neutralization to pH 7 with an aqueous 25% sodium hydroxide, to obtain 1903 parts by weight of wet DOG crystals. By vacuum-drying the wet DOG crystals, 1236 parts by weight of dried DOG was obtained. X was 21% by weight and the yield of DOG on the basis of the charged TMP was 83 mol %. The water content of the wet DOG crystals before drying was 35% (wet basis) and the average particle size of DOG obtained was 7 μm. The melting point of DOG obtained was 121.5° C. and the trans-isomer purity determined by GC analysis was 90%.

COMPARATIVE EXAMPLE 2

The procedures of Example 1 were repeated except for changing the amount of water from 3825 parts by weight to 961 parts by weight, to obtain 1882 parts by weight of wet DOG crystals. By vacuum-drying the wet DOG crystals, 1280 parts by weight of dried DOG was obtained. X was 40% by weight and the yield of DOG on the basis of the charged TMP was 85 mol %. The water content of the wet DOG crystals before drying was 32% (wet basis) and the average particle size of DOG obtained was 8 μm. The melting point of DOG obtained was 122.0° C. and the trans-isomer purity determined by GC analysis was 92%.

EXAMPLE 2

A reaction vessel was charged with 3825 parts by weight of water, 916 parts by weight of TMP and 100 parts by weight of concentrated hydrochloric, and the mixture was heated to 60° C. Into the reaction vessel, 1191 parts by weight of the crude HPA obtained in the same manner as in Example 1 was added over 3 h. After the dropwise addition, the reaction product liquid was aged for 2 h while maintaining the temperature at 60° C. to complete the reaction. Then, the neutralization, heating, cooling under stirring, and separation were performed in the same manner as in Example 1, to obtain 1406 parts by weight of wet DOG crystals. By vacuum-drying the wet DOG crystals, 1267 parts by weight of dried DOG was obtained. X was 21% by weight and the yield of DOG on the basis of the charged TMP was 85 mol %. The water content of the wet DOG crystals before drying was 10% (wet basis) and the average particle size of DOG obtained was 30 μm. The melting point of DOG obtained was 125.3° C. and the trans-isomer purity determined by GC analysis was 99.4%.

EXAMPLE 3

A reaction vessel was charged with 916 parts by weight of TMP and 3825 parts by weight of water, and the mixture was heated to 60° C. Into the reaction vessel, 1191 parts by weight of the crude HPA obtained in the same manner as in Example 1 and 100 parts by weight of concentrated hydrochloric acid were added respectively over 3 h. After the dropwise addition, the reaction product liquid was aged for 2 h while maintaining the temperature at 60° C. to complete the reaction. Then, the neutralization, heating, cooling under stirring, and separation were performed in the same manner as in Example 1, to obtain 1442 parts by weight of wet DOG crystals. By vacuum-drying the wet DOG crystals, 1240 parts by weight of dried DOG was obtained. X was 20% by weight and the yield of DOG on the basis of the charged TMP was 84 mol %. The water content of the wet DOG crystals before drying was 14% (wet basis) and the average particle size of DOG obtained was 23 μm. The melting point of DOG obtained was 125.3° C. and the trans-isomer purity determined by GC analysis was 99.4%.

EXAMPLE 4

A reaction vessel was charged with 1191 parts by weight of the crude HPA obtained in the same manner as in Example 1 and 3325 parts by weight of water, and the mixture was heated to 60° C. Into the reaction vessel, an aqueous solution containing 916 parts by weight of TMP and 500 parts by weight of water and 100 parts by weight of concentrated hydrochloric acid were added respectively over 3 h. After the dropwise addition, the reaction product liquid was aged for 2 h while maintaining the temperature at 60° C. to complete the reaction. Then, the neutralization, heating, cooling under stirring, and separation were performed in the same manner as in Example 1, to obtain 1443 parts by weight of wet DOG crystals. By vacuum-drying the wet DOG crystals, 1255 parts by weight of dried DOG was obtained. X was 21% by weight and the yield of DOG on the basis of the charged TMP was 85 mol %. The water content of the wet DOG crystals before drying was 13% (wet basis) and the average particle size of DOG obtained was 24 μm. The melting point of DOG obtained was 125.2° C. and the trans-isomer purity determined by GC analysis was 99.3%.

EXAMPLE 5

A reaction vessel was charged with 1191 parts by weight of the crude HPA obtained in the same manner as in Example 1 and 3325 parts by weight of water, and the mixture was heated to 60° C. Into the reaction vessel, 916 parts by weight of TMP, 500 parts by weight of water and 100 parts by weight of concentrated hydrochloric acid were respectively added over 3 h. After the dropwise addition, the reaction product liquid was aged for 2 h while maintaining the temperature at 60° C. to complete the reaction. Then, the neutralization, heating, cooling under stirring, and separation were performed in the same manner as in Example 1, to obtain 1448 parts by weight of wet DOG crystals. By vacuum-drying the wet DOG crystals, 1260 parts by weight of dried DOG was obtained. X was 21% by weight and the yield of DOG on the basis of the charged TMP was 85 mol %. The water content of the wet DOG crystals before drying was 13% (wet basis) and the average particle size of DOG obtained was 24 μm. The melting point of DOG obtained was 125.4° C. and the trans-isomer purity determined by GC analysis was 99.5%.

The high purity DOG produced by the process of the present invention is a polyhydric alcohol having a cyclic acetal structure, and is useful as an intermediate or a monomer for the production of polymeric materials such as poly(meth)acrylate, polycarbonate, polyester, polyurethane, polyether polyol and an epoxy resin, and also useful as a raw material for the production of a photo-curable resin, an adhesive, a photo-curable ink, a plasticizer, a resin stabilizer, a lubricant oil, a paint, etc.

What is claimed is:

1. A process of producing a dioxane glycol represented by the following formula I:

$$\text{(I)}$$

which comprises:

(1) a step of allowing hydroxypivalaldehyde represented by the following formula II:

$$\text{(II)}$$

to react with trimethylolpropane represented by the following formula III:

$$\text{(III)}$$

in a solvent in the presence of an acid catalyst, thereby obtaining a reaction product liquid containing the dioxane glycol of the formula I;

(2) a step of neutralizing the reaction product liquid;

(3) a step of heating the reaction product liquid after the neutralization to 70° C. or higher, thereby completely or partly dissolving crystals of the dioxane glycol; and (4) a step of cooling the reaction product liquid after the heating to 60° C. or lower, thereby allowing the dissolved dioxane glycol to recrystallize;

while regulating X represented by the following formula:

$$X(\% \text{ by weight}) = B/A \times 100$$

wherein A is a total weight of the reaction product liquid obtained in the step 1 and B is a theoretical amount of the dioxane glycol to be produced from hydroxypivalaldehyde and trimethylolpropane which are introduced into a reaction system, within a range of from 3 to 35% by weight.

2. The process according to claim 1, wherein the reaction product liquid is heated to 80 to 105° C. in the step 3.

3. The process according to claim 1, wherein the crystals of the dioxane glycol is completely dissolved in the step 3.

4. The process according to claim 1, wherein the reaction product liquid is cooled under stirring at a stirring rate of 0.5 m/s or more when expressed by a circumferential speed of a stirring blade tip in the step 4.

5. The process according to claim 1, wherein the reaction of hydroxypivalaldehyde and trimethylolpropane in the step 1 is performed by adding one of a solution of hydroxypivalaldehyde and a solid or solution of trimethylolpropane to the other over 0.5 h or more.

6. The process according to claim 5, wherein the solution of hydroxypivalaldehyde is added to the solution of trimethylolpropane containing the acid catalyst.

7. The process according to claim 5, wherein the solution of hydroxypivalaldehyde and the acid catalyst, which are kept apart from each other, are simultaneously added to the solution of trimethylolpropane.

8. The process according to claim 5, wherein the solid or solution of trimethylolpropane and the acid catalyst, which are kept apart from each other, are simultaneously added to the solution of hydroxypivalaldehyde.

9. The process according to claim 5, wherein a mixture of the solid or solution of trimethylolpropane and the acid catalyst is added to the solution of hydroxypivalaldehyde.

10. The process according to claim 5, wherein the addition is performed over 0.5 to 24 h.

11. The process according to claim 1, wherein the reaction of hydroxypivalaldehyde and trimethylolpropane in the step 1 is performed at 40 to 60° C.

* * * * *